US008247213B2

(12) United States Patent
Yih et al.

(10) Patent No.: US 8,247,213 B2
(45) Date of Patent: Aug. 21, 2012

(54) METHODS FOR MASSIVE CULTURE OF *DINOPHYSIS ACUMINATA* AND ISOLATION OF PECTENOTOXIN-2

(75) Inventors: WonHo Yih, Daejeon (KR); Jung-Rae Rho, Jeollbuk-do (KR); Hyung-Seop Kim, Jeollabuk-do (KR); HeonJoong Kang, Gyeonggi-do (KR)

(73) Assignee: Industry-Academic Cooperation Foundation, Kunsan National University, Jeollabuk-do (KR)

( * ) Notice: Subject to any disclaimer, the term of this patent is extended or adjusted under 35 U.S.C. 154(b) by 413 days.

(21) Appl. No.: 12/565,176

(22) Filed: Sep. 23, 2009

(65) Prior Publication Data

US 2010/0105928 A1 Apr. 29, 2010

(30) Foreign Application Priority Data

Sep. 25, 2008 (KR) ........................ 10-2008-0094357

(51) Int. Cl.
*C12N 1/10* (2006.01)
*C07D 493/22* (2006.01)

(52) U.S. Cl. ..................................... 435/258.1; 549/263

(58) Field of Classification Search ................ 435/258.1
See application file for complete search history.

(56) References Cited

OTHER PUBLICATIONS

M. Park et al., "First successful culture of the marine dinoflagellate *Dinophysis acuminata*", *Aquat Microb Ecol*, vol. 45:101-106, 2006.
W. Yih et al., "Ingestion of cryptophyte cells by the marine photosynthetic ciliate *Mesodinium rubrum*", *Aquat Microb Ecol*, vol. 36: 165-170, 2004.

*Primary Examiner* — Herbert J Lilling
(74) *Attorney, Agent, or Firm* — Clark & Brody

(57) ABSTRACT

Provided is a method for massive culture of *Dinophysis acuminata* which is a marine dinoflagellate causing diarrhetic shellfish poisoning, and methods for extracting, isolating and purifying the shellfish toxin pectenotoxin-2 from the cultured *Dinophysis acuminata*. Particularly, *Dinophysis acuminata* is cultured massively in massive culture apparatus comprising polycarbonate water bath having the bottom sinking down toward the center of the bottom; acryl tube (E) containing fluorescent lamp laid long in the center of the water bath; air supplying device (B) supplying the air to the sinking center of the bottom of the water bath; and air purifying device containing one or more devices selected from the group consisting of UV lamp (C) and carbon cartridge filter (D) purifying the air supplied by the said air supplying device.

3 Claims, 6 Drawing Sheets

| | $^{13}C$ | $^{1}H$ | | $^{13}C$ | $^{1}H$ |
|---|---|---|---|---|---|
| 1 | 173.9 | | 26 | 51.1 | 1.69(m); 1.54(m) |
| 2 | 49.1 | 2.30(dd, 9.3, 6.4) | 27 | 31.5 | 2.58(m) |
| 3 | 77.4 | 3.45(dd, 12.3, 12.3) | 28 | 141.2 | 5.26(d, 10.3) |
| 4 | 30.5 | 1.48(m)/1.14(m) | 29 | 131.8 | |
| 5 | 22.7 | 1.83(m)/1.54(m) | 30 | 136.1 | 6.47(dd, 15.7, 1.5) |
| 6 | 35.1 | 1.67(2H, m) | 31 | 122.3 | 5.41(dd, 15.7, 3.4) |
| 7 | 108.7 | | 32 | 84.0 | 4.75(q, 2.0) |
| 8 | 33.4 | 2.49(dd 12.2, 6.4); 1.54 | 33 | 76.02 | 5.45(dd, 3.4, 3.4) |
| 9 | 22.9 | 2.06(m)/1.64(m) | 34 | 34.2 | 2.19(d, 12.7, 3.9); 2.09 |
| 10 | 81.9 | 4.28(br d, 6.4) | 35 | 82.9 | 4.49(dd, 10.8, 5.9) |
| 11 | 76.04 | 4.00(d, 1.5) | 36 | 98.6 | |
| 12 | 82.6 | | 37 | 71.6 | 3.27(m) |
| 13 | 44.7 | 2.85(d, 16.1); 1.97(d,16.1) | 38 | 30.6 | 2.11(m) |
| 14 | 214.6 | | 39 | 28.2 | 1.66(m); 1.24(m) |
| 15 | 80.1 | 3.80(d, 1.5) | 40 | 61.8 | 3.96(dd, 11.3, 2.5) |
| 16 | 72.0 | 4.25(ddd, 12.7,3.9,1.5) | | | 3.67(dd, 11.3, 4.9) |
| 17 | 36.9 | 2.06(m); 1.30(m) | 41 | 15.9 | 1.07(d, 6.9) |
| 18 | 81.6 | | 42 | 23.3 | 1.19(d, 7.3) |
| 19 | 34.4 | 1.89(m); 1.66(m) | 43 | 26.1 | 1.32(s) |
| 20 | 28.9 | 2.17(m); 1.97(m) | 44 | 26.7 | 1.20(s) |
| 21 | 110.2 | | 45 | 23.8 | 0.96(d, 6.4) |
| 22 | 80.2 | 3.84(dd,10.3, 5.9) | 46 | 12.8 | 1.68(s) |
| 23 | 30.2 | 2.01(m); 1.65(m) | 47 | 17.9 | 0.93(d, 6.9) |
| 24 | 38.2 | 1.61(m); 1.41(m) | | | |
| 25 | 86.2 | | | | |

METHODS FOR MASSIVE CULTURE OF *DINOPHYSIS ACUMINATA* AND ISOLATION OF PECTENOTOXIN-2

CROSS-REFERENCE(S) TO RELATED APPLICATIONS

The present invention claims priority of Korean Patent Application No. 10-2008-0094357, filed on Sep. 25, 2008, which is incorporated herein by reference.

BACKGROUND OF THE INVENTION

1. Field of the Invention

The present invention relates to a method for massive culture of *Dinophysis acuminata*, the marine dinoflagellate causing diarrhetic shellfish poisoning, and methods for extracting, isolating and purifying the shellfish toxin pectenotoxin-2 from the cultured *Dinophysis acuminata.*

2. Description of Related Art

*Dinophysis* sp. belonging to dinoflagellates causing red tide is known to produce pectenotoxin (PTX) which is one of diarrhetic shellfish toxins. Once this organism causes red tide in the ocean, it brings huge damage on marine shellfish aquaculture. The major toxins produced by this living thing are okadaic acid, pectenotoxin, dinophysistoxin and yessotoxin, etc. It has been recently reported that pectenotoxin induces apoptosis selectively of cancer cells. So, expectation of medical or pharmaceutical usability of this material is increasing. In addition, pectenotoxin can be used as a standard material for toxin especially when red tide occurs by this living thing in the ocean. Although pectenotoxin has a wide spectrum of application, studies on the material have been limited for a long time because massive-culture of *Dinophysis* was unsuccessful and thus pectenotoxin could only picked up from a limited area.

*Dinophysis acuminate*, the marine dinoflagellate is a causing organism of diarrhetic shellfish poisoning which could not be cultured successfully in a lab until the year of 2006. The culture of *Dinophysis acuminate* was first succeeded by supplying laboratory culture of *Myrionecta rubra*, a marine ciliate, as feed in 2006 (Park et al. 2006. First successful culture of the marine dinoflagellate *Dinophysis acuminate*. Aquat. Microb. Ecol. 45, 101-106). Since then, success of culture of *Dinophysis acuminate* or other *Dinophysis* species using *Myrionecta rubra* has been reported from time to time.

However, the marine dinoflagellate, *Dinophysis acuminate* has been cultured only in a laboratory scale. So, the culture amount of *Dinophysis acuminate* is always not enough for the study of pectenotoxin, considering the increasing medical or pharmaceutical usability of the material. Therefore, a method for massive culture of *Dinophysis acuminate* is urgently requested for the study of pectenotoxin.

Based on the early method for culture of a small amount of *Dinophysis acuminate*, which was succeeded in a lab, the present inventors designed a simple water bath for massive culture of 500 liter and tried to establish a method for culture of the organism and a method for extracting and separating pectenotoxin, the diarrhetic shellfish toxin contained in the organism.

SUMMARY OF THE INVENTION

An embodiment of the present invention is directed to providing a method for massive culture of *Dinophysis acuminate.*

Another embodiment of the present invention is directed to providing a method for extracting and separating/purifying pectenotoxin-2 (PTX-2), the intracellular toxin of *Dinophysis acuminate.*

To achieve the objects of the present invention, the present invention provides a method for massive culture of *Dinophysis acuminate*, the marine dinoflagellate causing diarrhetic shellfish poisoning, and methods for extracting and separating/purifying pectenotoxin-2, the shellfish toxin included in *Dinophysis acuminate.*

Hereinafter, the present invention is described in detail.

The present invention relates to a method for massive culture of *Dinophysis acuminate*, the marine dinoflagellate causing diarrhetic shellfish poisoning, composed of the following 4 steps.

1) sub-culturing *Myrionecta rubra* at 10~30° C. with continuous light, for which *Myrionecta rubra* and its prey *Teleaulax* are inoculated in sea water medium at the density ratio of 1:10-1:15;

2) inoculating *Myrionecta rubra* cultured in step 1) in the water bath supplied with the air purified by carbon cartridge filter after irradiation, and then mass-culturing *Myrionecta rubra* with stirring the cultured *Myrionecta rubra* in step 1) and the sea water medium using air bubbles formed and supplied through air sparging nozzle equipped on the lower part of the water bath at 10~30° C. with continuous light;

3) inoculating *Dinophysis acuminata* and *Myrionecta rubra*, the prey for *Dinophysis acuminata*, at the density ratio of 1:10-1:30, followed by sub-culturing of *Dinophysis acuminata* at 10~30° C. with continuous light;

4) mass-culturing *Dinophysis acuminata* by inoculating the *Dinophysis acuminata* cultured in step 3) in the water bath of step 2).

The sea water medium used for the massive culture of Dinophysis acuminata of the present invention includes any conventional medium used for the culture of algae except diatoms, for example f/2-Si medium, particularly 30 psu (practical salinity unit) f/2-Si medium.

The massive culture apparatus for massive culture of *Dinophysis acuminata* comprising 500 liter water bath and its parts are illustrated in FIG. 1. This apparatus for massive culture of *Dinophysis acuminata* can also be used for massive culture of other kinds of plant planktons.

Massive culture of *Dinophysis acuminata* of the present invention, particularly massive culture in step 2) or step 4) is performed in massive culture apparatus comprising polycarbonate water bath having the bottom sinking down toward the center of the bottom; acryl tube (E) containing fluorescent lamp laid long in the center of the water bath; air supplying device (B) supplying the air to the sinking center of the bottom of the water bath; and air purifying device containing one or more devices selected from the group consisting of UV lamp (C) and carbon cartridge filter (D) purifying the air supplied by the said air supplying device (FIG. 1).

The water bath of the massive culture apparatus has the volume of at least 500 liter and is made round of more than 0.8 m diameter from polycarbonate plate emitting least toxic materials, whose bottom is sinking to the center of the bottom part. This water bath, therefore, suits for harvest of *Dinophysis acuminata* massively cultured and is easy to clean and drain. The top of the bath is covered by a lid to prevent foreign materials from coming in. The height of the bath is at least 1 m. The ratio of cylindrical part to conical part is 2:1-3:2. The diameter of this bath is at least 0.8 m, which favors receiving light enough.

This apparatus also contains culture medium for massive culture, precisely sea water medium, and acryl tube with a built-in fluorescent lamp (32 watt, 120 cm long) laid long in the center of the bath to supply light to the target organism evenly, which makes the plant do photosynthesis effectively. It also includes air supplying device (B) composed of air supplying part supplying air to the sinking center part of the bottom of water bath, connection tube and sparging nozzle, and air purifying device containing one or more devices selected from the group consisting of UV lamp and carbon cartridge filter (D) purifying the air supplied by the said air supplying device.

Small bubbles are formed from the sinking center part of the bottom of the water bath by the sparging nozzle in the air supplying device.

*Dinophysis acuminata* massively cultured by the said method can be recovered by ultra centrifuge (F) connected to the sinking center part of the bottom of the water bath.

The result of massive culture of *Dinophysis acuminata* using the massive culture apparatus of the present invention is illustrated in FIG. 2.

In the method of the present invention, to culture *Dinophysis acuminata* and its prey *Myrionecta rubra* massively, 100 Mℓ of seed strain was first cultured to 2 ℓ, followed by subculture as follows; 2 ℓto 20 ℓand 20 ℓto 500 ℓ. At this time, inoculation ratio of *Myrionecta rubra* to its prey *Teleaulax* was 1:10-1:15 and inoculation ratio of *Dinophysis acuminata* to its prey *Myrionecta rubra* was 1:10-1:30. To increase maximum density of *Dinophysis acuminata,* ⅕ of sea water medium was discarded when the prey *Myrionecta rubra* was consumed and then fresh sea water medium was preferably added together with *Myrionecta rubra* the prey thereto.

Further, the present invention provides methods for harvesting *Dinophysis acuminata* massively cultured from the sea water medium using ultra centrifuge (F) connected to the fallen center part of the bottom of the water of the massive culture apparatus, for separating and purifying the toxin, pectenotoxin-2 (FIG. 3), from the harvested *Dinophysis acuminata* using solvent distribution and chromatography. The separated and purified pectenotoxin-2 was confirmed by mass spectrometer and NMR. The mass analysis data obtained therefrom (FIG. 4) and hydrogen and carbon spectrums (FIG. 5 and FIG. 6) are shown in the attached Fig.s and chemical shifts of hydrogen and carbon of pectenotoxin-2 are shown in FIG. 7.

The solvent distribution herein is performed by the following steps: extracting with solvent using butanol solution; concentrating the alcohol extract, followed by solvent fractionation using methanol/water/-n-hexane mixture composed of the volume ratio of 1:5~6:6~7; and concentrating the solvent fractionated layer composed of methanol and water. Upon completion of the solvent distribution, chromatography is performed. Precisely reverse-phased silica flash chromatography and reverse-phased semi-preparative HPLC are performed stepwise to separate/purify pectenotoxin-2.

Reverse-phased silica flash chromatography uses reverse phase silica gel as immobile phase and uses water/methanol (1:1~9, V/V) mixture, methanol and acetone as eluents. More preferably, the mixture of water and methanol (1:4, V/V) is used as eluent. Effluent from reverse-phased silica flash chromatography is concentrated, followed by reverse-phased semi-preparative HPLC using column filled with reverse-phased silica gel (C18) and eluent which is the mixture of methanol (75%) and water (25%). Pectenotoxin-2 is extracted at retention time of 59 minutes.

DESCRIPTION OF SPECIFIC EMBODIMENTS

The advantages, features and aspects of the invention will become apparent from the following description of the embodiments with reference to the accompanying drawings, which is set forth hereinafter.

Example 1

Massive Culture of *Dinophysis Acuminate*

To culture *Dinophysis acuminate*, the ciliate *Myrionecta rubra* the prey for *Dinophysis acuminate*, and the cryptomonad *Teleaulax*, the prey for *Myrionecta rubra*, had to be first cultured enough. For the culture of these two preys, the present inventors referred the literature (Yih et al. 2004. Ingestion of cryptophyte cells by the marine photosynthetic ciliate *Mesodinium rubrum*. Aquat. Microb. Ecol. 36:165-170) informing the size of experiment (small scale, 500 Mℓ) and then cultured 100 Mℓsized laboratory seed strain up to 2 ℓwhich was then sub-cultured to 20 ℓ. The cultured seed strain was inoculated in massive culture apparatus containing 500 ℓwater bath and grown for 1 week until *Dinophysis acuminate* was inoculated. At that time, the ratio of the seed strain to its prey *Teleaulax* was 1:10-1:15. The culture was performed in f/2-Si medium at 20° C. with salt concentration of 30 psu and with continuous light at the luminosity of 60 photon/$m^2$/sec. The seed strain was sub-cultured when the maximum cell density reached 10,000 cells/Mℓ.

Figure 1:
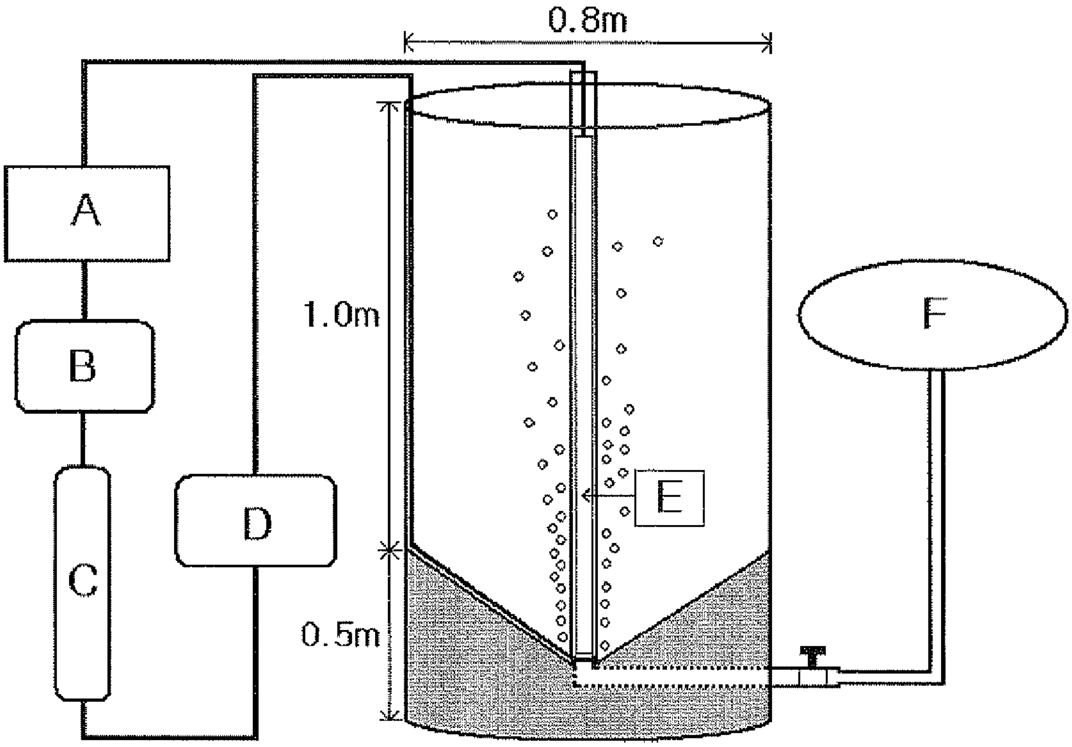
FIG. 1 illustrates the 500 ℓmassive culture apparatus for *Dinophysis acuminata* culture. A: power supply, B: air supplying device to supply air, C: UV lamp to sterilize the supplied air, D: carbon cartridge filter to filter the supplied air, E: 32 watt fluorescent lamp, and F: ultra centrifuge to harvest the cultured organism.
Figure 2:
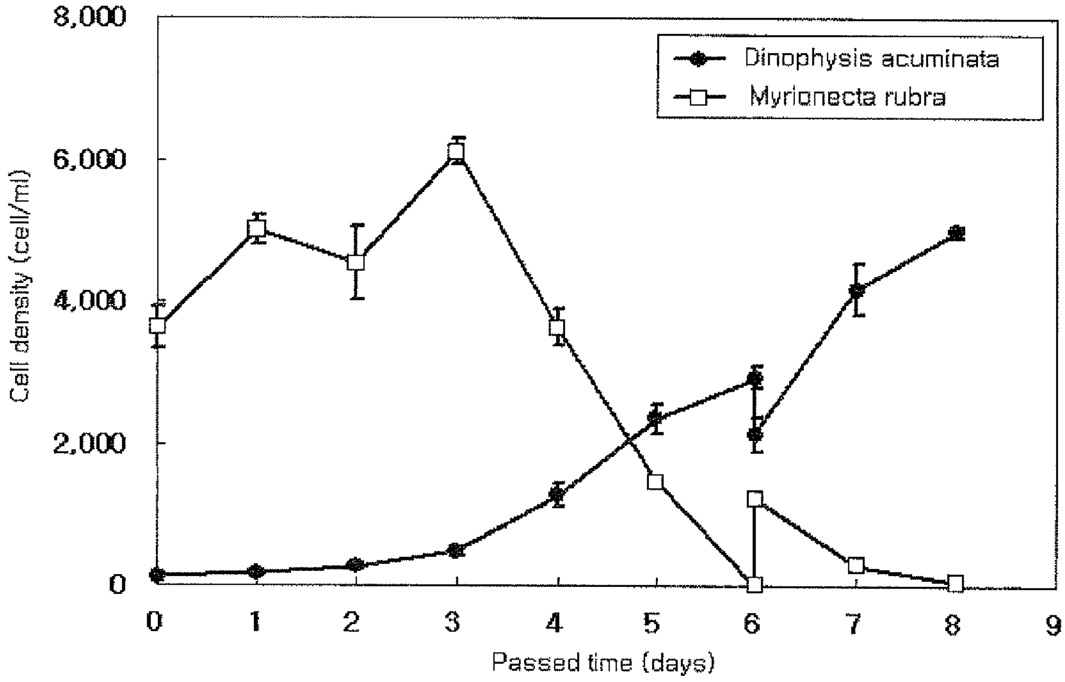
FIG. 2 is a graph illustrating the changes of cell densities of *Dinophysis acuminata* and the prey *Myrionecta rubra* observed for 8 days of massive culture (500 ℓ) of *Dinophysis acuminata* in Example 1.
Figure 3:
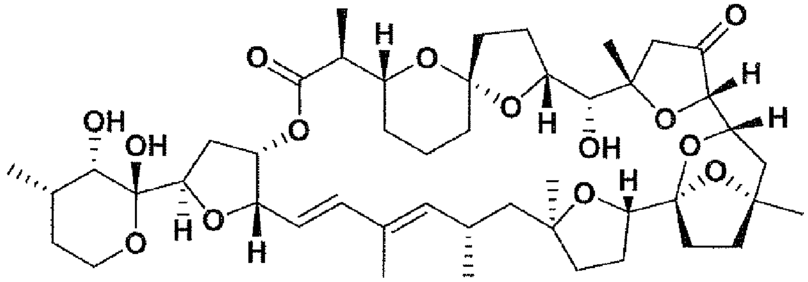
FIG. 3 illustrates the chemical structure of the pectenotoxin-2 separated and purified from *Dinophysis acuminata.*

For massive culture of *Dinophysis acuminata* with 500 ℓscale, small scale (100 Mℓ) of laboratory seed strain was first cultured with increasing the volume from 2 ℓto 20 ℓgradually. The ratio of *Dinophysis acuminata* to its prey *Myrionecta rubra* was adjusted to 1:30 at the initial inoculation. Subculture interval was 5-10 days. When the maximum density of *Dinophysis acuminata* reached 2,000 cells/Mℓ, it was inoculated into a larger culture vessel. The culture was performed in f/2-Si medium at 20° C. with salt concentration of 30 psu and with continuous light at the luminosity of 60 photon/$m^2$/sec. When *Dinophysis acuminata* grew to 20 ℓ, it was inoculated into the massive culture apparatus containing 500 ℓwater bath wherein the prey *Myrionecta rubra* had been growing for a week. On day 6, when the prey *Myrionecta rubra* was all consumed and the density of *Dinophysis acuminata* reached about 3,000 cells/Mℓ, ⅕ of sea water medium was discarded and *Myrionecta rubra* which was growing in a separate 20 ℓculture vessel was supplied and fresh sea water medium was also added. Then, when the maximum density of *Dinophysis acuminata* reached about 5,000 cells/Mℓ, harvest was performed (FIG. 2).

Example 2

Separation and Purification of Pectenotoxin-2 from *Dinophysis acuminata*

After culturing *Dinophysis acuminata* to 500 ℓin a lab, 100 g (wet weight) of the biomass was harvested using continuous centrifuge (flow rate: 3 ℓ/min, 6000 rpm). The obtained organism was freeze-dried for 3 days, then 3.0 ℓof methanol was added thereto, which stood for 48 hours, followed by extracting organic material. The solvent was removed from the extract using rotary evaporator, to which the mixed solution composed of butanol and water (1:1) was added, followed by solvent distribution to separate water layer and butanol layer. Butanol was eliminated from the butanol layer obtained by the solvent distribution using vacuum evaporator, to which the mixture composed of methanol (15%) and water (85%) and n-hexane (1:1) were added, followed by redistribution. Next, the solvent layer composed of methanol and water was separated, and then the solvent was eliminated by the same method described above. The obtained fraction proceeded to reverse-phased silica flash chromatography. At this time, reverse-phased silica gel (C-18) was used as immobile phase. The eluent was used in the order of high polarity to lower polarity. Particularly, the order was as follows and the amount of organic material obtained was as described: 50% water/50% methanol (300 mg), 40% water/60% methanol (200 mg), 30% water/70% methanol (10 mg), 20% water/80% methanol (10 mg), 10% water/90% methanol (50 mg), 100% methanol (240 mg), 100% acetone (230 mg). Spectrum was measured with each fraction obtained by the above method using hydrogen NMR spectrometer. As a result, it was confirmed that approximately 70% of pectenotoxin-2 was included in the layer of 20% water/80% methanol. So, organic solvent was eliminated from the fraction containing pectenotoxin-2 using vacuum evaporator, followed by reverse-phased semi-prep HPLC to purify the major component pectenotoxin-2. Conditions for HPLC were as follows. column: YMC ODS-C18, particle diameter: 5 μm, column size: 250 10 mm (length diameter), elution rate: 1.5 Mℓ/min, detector: refractive index detector, and eluent: 75% methanol/25% $H_2O$. As a result, grey powder pectenotoxin-2 was separated at retention time of 59 minutes.

Figure 4:
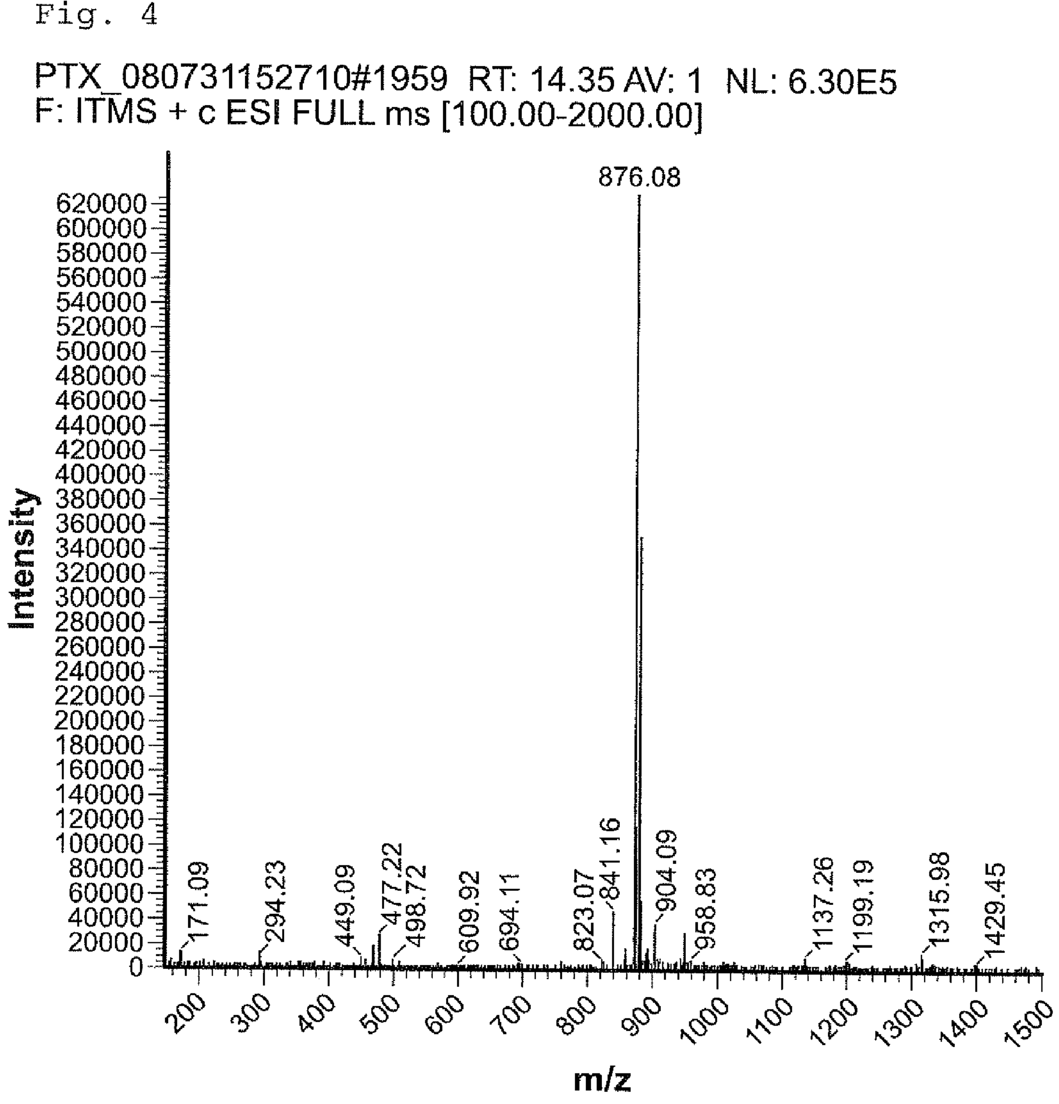
FIG. 4 illustrates the mass spectrometry data of the pectenotoxin-2 separated and purified in Example 2.
Figure 5:
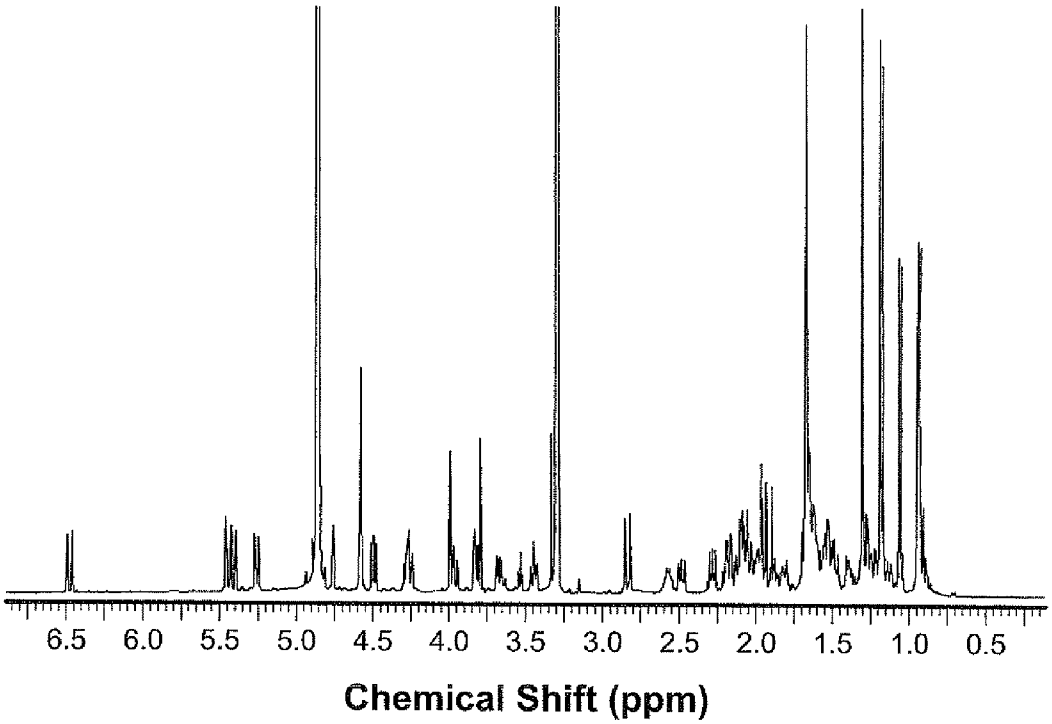
FIG. 5 illustrates the hydrogen NMR spectrometry data of the pectenotoxin-2 separated and purified in Example 2.
Figure 6:
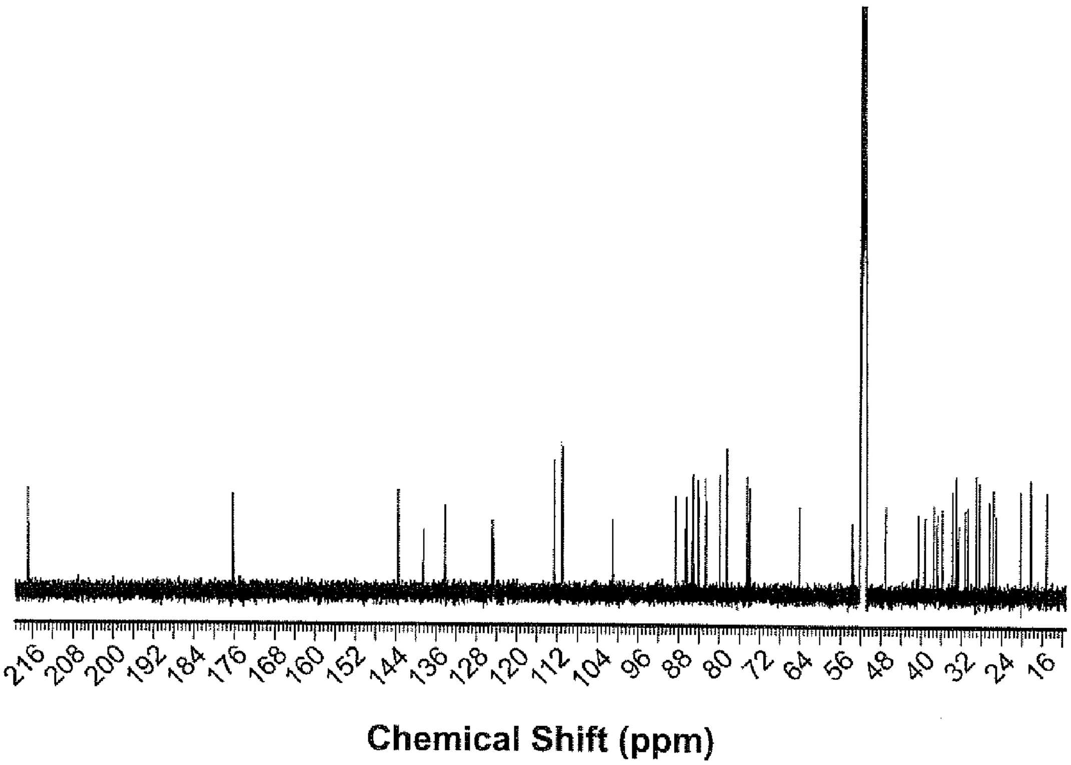
FIG. 6 illustrates the carbon NMR spectrometry data of the pectenotoxin-2 separated and purified in Example 2.
Figure 7:
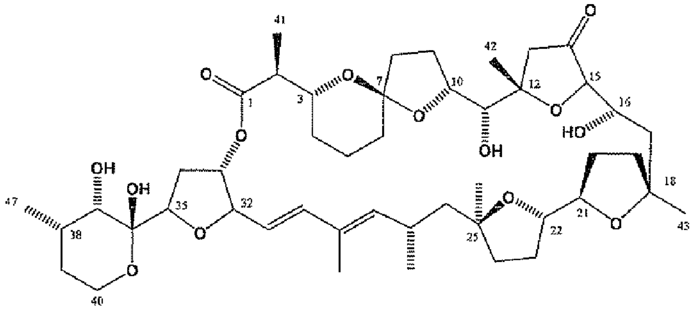
FIG. 7 is a table showing the hydrogen and carbon NMR lines designated in the molecular structure of the pectenotoxin-2 separated and purified in Example 2.

To confirm the pectenotoxin-2 finally obtained, liquid chromatography-mass spectrometer (LC-MS) and nuclear magnetic resonance (NMR) spectrometer were used. From the liquid chromatography-mass spectrometry was confirmed the molecular weight signals indicating pectenotoxin having the molecular weight of 858 and the one containing $H_2O$ and thus having the molecular weight of 876 ($M+H_2O$). 1D and 2D NMR spectrometry was performed with pectenotoxin-2 to identify the chemical structure, which was as described previously. Liquid chromatography-mass spectrometry data (FIG. 4) and hydrogen and carbon NMR spectrums (FIG. 5 and FIG. 6) were presented. FIG. 7 illustrates signals shown on hydrogen and carbon NMR spectrums of pectenotoxin-2.

Owing to the method for massive culture of *Dinophysis acuminata* of the present invention, the inventors succeeded the culture of *acuminata*, one of *Dinophysis* species, up to 500 liter, which had been unsuccessful until then. Pectenotoxin separated from *Dinophysis acuminata* can be not only used as a standard toxin for the analysis of toxins but also used for the study to fight cancer which is actively going on more than ever, suggesting that this material is a promising candidate for the medically pharmaceutically usable material.

While the present invention has been described with respect to the specific embodiments, it will be apparent to those skilled in the art that various changes and modifications may be made without departing from the spirit and scope of the invention as defined in the following claims.

What is claimed is:

1. A method for massive culture of *Dinophysis acuminate*, comprising;

sub-culturing *Myrionecta rubra* at 10~30° C. with continuous light, for which *Myrionecta rubra* and its prey *Teleaulax* are inoculated in sea water medium at the density ratio of 1:10-1:15;

inoculating *Myrionecta rubra* cultured in the sub-culturing of *Myrionecta rubra* in the water bath supplied with the air purified by carbon cartridge filter after irradiation, and then mass-culturing *Myrionecta rubra* with stirring the cultured *Myrionecta rubra* in the sub-culturing of *Myrionecta rubra* and the sea water medium using air bubbles formed and supplied through air sparging nozzle equipped on the bottom part of the water bath at 10~30° C. with continuous light;

inoculating *Dinophysis acuminate* and *Myrionecta rubra*, the prey for *Dinophysis acuminate*, at the density ratio of 1:10-1:30, followed by sub-culturing of *Dinophysis acuminate* at 10~30° C. with continuous light; and mass-culturing *Dinophysis acuminate* by inoculating the *Dinophysis acuminate* cultured in the sub-culturing of *Dinophysis acuminate* in the water bath of the mass-culturing of *Myrionecta rubra.*

2. The method for massive culture of *Dinophysis acuminate* according to claim 1, wherein the sea water medium is f/2-Si.

3. The method for massive culture of *Dinophysis acuminata* according to claim 1, wherein the massive culture in the mass-culturing of *Myrionecta rubra* or the mass-culturing of *Dinophysis acuminata* is performed in massive culture apparatus comprising polycarbonate water bath having the bottom sinking down toward the center of the bottom; acryl tube (E) containing fluorescent lamp laid long in the center of the water bath; air supplying device (B) supplying the air to the sinking center of the bottom of the water bath; and air purifying device containing one or more devices selected from the group consisting of UV lamp (C) and carbon cartridge filter (D) purifying the air supplied by the said air supplying device.

* * * * *